United States Patent [19]

McLaughlin

[11] Patent Number: 4,683,196
[45] Date of Patent: Jul. 28, 1987

[54] METHOD AND MATERIALS FOR THE IDENTIFICATION OF LIPOPOLYSACCHARIDE PRODUCING MICROORGANISMS

[75] Inventor: Charles A. McLaughlin, Berkeley, Calif.

[73] Assignee: Meru, Inc., Berkeley, Calif.

[21] Appl. No.: 590,211

[22] Filed: Mar. 16, 1984

Related U.S. Application Data

[63] Continuation-in-part of Ser. No. 560,123, Dec. 12, 1983, abandoned.

[30] Foreign Application Priority Data

Dec. 12, 1983 [CA] Canada .................................. 443090

[51] Int. Cl.⁴ .................... G01N 33/569; C12N 15/00; C12N 5/00; A61K 39/40
[52] U.S. Cl. ...................................... 435/7; 435/172.2; 435/240; 435/948; 435/810; 436/511; 436/548; 436/807; 530/387; 530/808; 530/809; 935/103; 935/110
[58] Field of Search .................. 435/7, 18, 21, 34, 35, 435/38, 39, 68, 172.2, 240, 810, 948; 438/548, 511, 807; 260/112 B, 112 R; 935/95, 102, 103, 106, 110; 530/387, 808, 809

[56] References Cited

U.S. PATENT DOCUMENTS

| | | | |
|---|---|---|---|
| 3,891,508 | 6/1975 | Merrick .................................. | 435/34 |
| 4,115,543 | 9/1978 | Wallace et al. ...................... | 436/511 |
| 4,376,110 | 3/1983 | David et al. ............................ | 435/7 |
| 4,427,782 | 1/1984 | Caldwell et al. ................ | 260/112 R |
| 4,471,058 | 9/1984 | Smith et al. .......................... | 436/548 |

OTHER PUBLICATIONS

Nurminen et al., Science, 220: 1279–1281 (Jun. 17, 1983).
Stevens et al., J. Immunol. Methods, 43: 199–207 (1981).
Caldwell et al., J. Immunol., 115(4): 963–968 (1975).
Apicella et al., Infect. Immun., 34(3): 751–756 (1981).
Hiernaux et al., Eur. J. Immunol., 12: 797–803 (1982).
Sugasawara et al., Infect. Immun., 43(3): 863–868 (1983 Dec.).
Puolakkainen, Mirja, et al., "Chlaymdial Pneumonitis and its Serodiagnosis in Infants" *The Journal of Infectious Diseases*, vol. 149, No. 4, Apr. 1984.
Nurminen, Marjatta, et al., "*Immunologically Related Ketodeoxyoctanate-Containing Structures in Chlamydia trachomatic*, Re Mutants of Salmonella Species, and *Acinetobacter calcoaceticus* Var. anitratus", Infection and Immunity, vol., 44, No. 3, Jun. 1984, pp. 609–613.
Caldwell, Harlan D., "Monoclonal Antibody Against a Genus-Specific Antigen of Chlamydia Species: Location of the Epitope on Chlamydial Lipopolysaccharide" Infection and Immunity, vol. 44, No. 2, May 1984, pp. 306–314.

*Primary Examiner*—Esther M. Kepplinger
*Attorney, Agent, or Firm*—Scully, Scott, Murphy & Presser

[57] ABSTRACT

The subject invention provides a means for the immunological detection of an entire class of microorganisms in clinical samples. The detection is accomplished by reaction of the clinical sample iwth a class-specific immunological reagent. This reagent is an antiserum either monoclonal or polyclonal in nature, and the detection is based upon reaction of the antiserum with an antigenic determinant which is shared among all members of the detectable class of microorganisms. The presence of the resulting immunological reaction product (e.g. the antigen-antibody complex) may be detected by well-known immunological detection-systems.

38 Claims, No Drawings

METHOD AND MATERIALS FOR THE IDENTIFICATION OF LIPOPOLYSACCHARIDE PRODUCING MICROORGANISMS

This application is a continuation-in-part of Ser. No. 560,123, filed Dec. 12, 1983, now abandoned.

FIELD OF THE INVENTION

This invention relates to the immunological detection of microorganisms. More specifically, the invention relates to methods and materials useful for the detection of a diverse group of microorganisms in a clinical sample.

BACKGROUND OF THE INVENTION

Microorganisms possessing a cell-surface component known as an endotoxic lipopolysaccharide (LPS) have been identified as the etiologic agents in a wide variety of diseases. Of particular interest are strains of the genera *Neisseria*, and *Chlamydia*, which are associated with certain venereal diseases; the incidence of these diseases having reached almost epidemic proportions The LPS molecule has been the subject of intense study. See for example, Westphal et al , *Bacterial Lipopolysaccharides,* Methods of Carbohydrate Chemistry, Vol. V, Academic Press, (1965), pgs 83–91; and Galanos et. al., *Biochemistry of Lipids II,* T. W. Goodwin (Ed), Univ. Park Press, (1977), Vol. 14, at page 239.

The structure of the lipopolysaccharide has been described in studies of Gram-negative bacteria such as, *Escherichia coli* and *Salmonella typhimurium.* In general, the antigen can be visualized as possessing three component regions. Proximal to and imbedded into the outer portion of the cell membrane is the so-called lipid A component. This component has been associated with the endotoxin properties of the molecule and is believed to be a highly conserved sequence; that is to say, a wide variety of organisms would likely possess identical lipid A regions. The middle region of the LPS molecule is another conserved region, the so-called core oligosaccharide. The core oligosaccharide is bipartite in structure based upon the types of sugar moieties of which it is composed. The innermost region which is adjacent to the lipid A component contains the unusual sugar, 3-deoxy-manno-octulosonic acid, also known as ketodeoxyoctanoic acid (KDO). The outermost region of the core structure is comprised of a region of seven-carbon sugars (heptoses) which is followed distally by a region containing six-carbon sugars (hexoses). The most distal region of the LPS molecule is the so-called somatic or (0) region comprised of highly-variable polysaccharide components.

It is this outermost region which induces the strongest immune response in infected organisms and it is to this region that antisera produced thereby is directed. Thus, even though a number of different taxa may possess the same Lipid A and core components of the LPS molecules, because of the antigenic variability of the somatic region, antisera produced thereto will be specific for each type of inducing organism.

Microorganisms can thus be classified into chemotypes based upon their carbohydrate composition in the 0 region of the LPS. One method is described by Merrick in U.S. Pat. No. 3,891,508. Such a composition analysis although somewhat useful for purposes of identification is limited by not being able to discriminate between two organisms which may possess the same kinds of sugars but in different proportions or in different sequences.

The LPS molecule when used as an immunogen, may produce certain toxic side-effects due to the biological activity of the molecule. Several patents, such as U.S. Pat. Nos. 4,185,090 and 4,057,685 relate to methods of reducing the toxicity of the molecule but retaining the antigenicity of the O region. The specificity of the O region in permitting the identification, of only a single species is disclosed by Wallace et. al. in U.S. Pat. No. 4,115,543 relating to the identification of *Neisseria gonorrhoeae*. Other approaches attempt to find other antigenic inducers and eliminate the LPS molecule from the immunizing mixture as for example, described by Ayme in U.S. Pat. No. 4,337,243.

It has been recently demonstrated that conventional polyclonal sera raised to *Salmonella typhimuruin* Re mutants cross-react with various *Chlamydia* species (Nurminen, et al., *Science* 220: 1279–81 (1983)). There is no suggestion of the diagnostic utility nor of the wider reactive potential of the antibodies as produced and described hereinbelow.

Human monoclonals of the $IgG_1$ subclass have been demonstrated to be reactive with a limited class of microorganisms namely members of the Chlamydia genera. Although, not particularly well-characterized, the antigen to which the monoclonals are directed is referred to as a lipoprotein complex. Thus, it is probably closely related to the *Chlamydia* group specific protein as characterized by Caldwell, et al., (J. Immuno. 115: 963-68 (1975)) and clearly distinct from the endotoxic-glycolipid as described herein.

In an interesting, but unrelated application, (PCT application No. WO80/001109) the LPS molecule itself has been used as a marker reagent; being chemically attached to a ligand, it permits the detection of the LPS-ligand complex by standard LPS assay method (The Limulus amebocyte assay).

None of the above references relate to the object of the subject invention, that being, the generation of immunological reagents useful in the identification of a diverse group of LPS producing microorganisms.

BRIEF DESCRIPTION OF THE INVENTION

The subject invention provides a means for the immunological detection of an entire class of microorganisms in clinical samples. The detection is accomplished by reaction of the clinical sample with a class-specific immunological reagent. This reagent is an antiserum either monoclonal or polyclonal in nature, and the detection is based upon reaction of the antiserum with an antigenic determinant which is shared among all members of the detectable class of microorganisms. The presence of the resulting immunological reaction product (e.g. the antigen-antibody complex) may be detected by well-known immunological detection systems employing analytically indicatable reagents.

The subject invention is particularly useful for the detection of a class of microorganisms which produce endotoxin or endotoxin-like molecules. The shared antigen determinant in this case, is often a component of a cell-surface lipopolysaccharide. Microorganisms which display this antigen and thus are members of a detectable group comprise Chlamydia, Rickettsia, and other gramnegative microorganisms such as Neisseria, Brucella, Escherichia, Salmonella and the like.

In a preferred embodiment, an antibody to the shared determinant of the detectable class is used as the "capture" antibody in a differential screening assay system. Once recovered from a clinical sample as a member of the reactive class of microbes which possess the shared antigen, the captured cells or antigens are then subsequently reacted with more specific antisera to indicate which particular genera, species or serotype of microorganism is present.

For example, a first antibody is synthesized which reacts with the "gram-negative-like" portion of the endotoxic glycolipid, and second antibody is synthesized which reacts with a Chlamydial genus specific determinant. The first antibody can be used alone to detect all gram-negative-like microorganism by simple fluorescent or agglutination assays. Alternatively, the two antibodies may be used in combination in a solid phase immunoassay to discriminate the Chlamydia genera from among the other members of the reactive class.

In a further embodiment, the Chlamydia genus specific antibody may be used alone to detect all members of the Chyamdia genus or as the capture antibody in a differential screening assay whereby the Chlamydia genus specific antibody is used to react with all members of the genus and a second antibody or antibodies which are reactive to Chlamydia species determinants are employed to differentiate each species in the reactive genera.

The subject invention provides an immunological reagent for the detection of shared antigenic determinants of at least two microorganisms comprising an antibody specifically reactive to said shared determinants, more specifically an immunological reagent for the detection of two or more endotoxin or endotoxin-like lipopolysaccharide-producing microorganisms comprising a monoclonal antibody specifically reactive with shared antigenic determinants of said lipopolysaccharide.

Also provided are methods for the immunological detection of an antigen shared by a plurality of taxonomically distinct microorganisms. One such method comprises: contacting a sample containing said microorganisms or antigens thereof with an analytically indicatable antibody to form an immunocomplex of said microorganism or antigen thereof and said antibody, said antibody being characterized as having affinity for an antigenic determinant shared by said microorganism. There is also provided a two-site immunometric assay to identify an antigen in a sample comprising forming a ternary complex of a first labelled antibody, said antigen, and a second antibody, said second antibody being bound to a solid carrier insoluble under ternary complex forming conditions wherein the presence of the antigen is detected and identified by measuring either the amount of labelled antibody bound to said solid carrier or the amount of unreacted labelled antibody, in which the improvement comprises employing as said second antibody a monoclonal antibody characterized in having affinity for an antigenic determinant site of said antigen which is shared by a plurality of taxonomically distinct microorganisms and employing as a first antibody an antibody characterized as having an affinity for an antigenic determinant site specific to a taxonomically distinct microorganism.

DETAILED DESCRIPTION OF THE INVENTION

This invention provides reagents and methods for the detection and subsequent differential identification of an entire class of microbes. For the purposes of this description, class is not used in its strict biological/taxonomic meaning but rather in a more general sense referring to a group of microorganisms that express a common antigenic determinant. The terms antigenic determinant, antigenic determinant site (ADS) or epitope as used throughout, refer to a limited, specific part of an antigen which is the inducer of antibody formation and which is the region of the antigen to which the induced antibody reacts. The number of antigenic determinant sites possessed by a given antigen will vary and may range from 1 to 10 or 20 or more depending upon the size and immunological complexity of the antigen molecule. Those antigenic determinants which are unique to a given antigen are known as specific determinants and are useful in discriminating between two different types of antigen molecules. Those determinants which are present on two or more antigens are known as shared determinants and, as mentioned above, form the basis of an immunological class of antigens.

An antigen of particular interest with respect to the subject invention, as described above, is the lipopolysaccharide (LPS)/glycolipid antigen associated with endotoxin or endotoxin-like molecules produced by Gram-negative microorganisms.

With reference to the discussion of antigenic determinants above, each of the three regions of the LPS/glycolipid molecule could be considered to be comprised of one or more separate ADSs. The somatic region is considered to be a specific determinant since, because of its high variability, antibodies raised to the somatic region of one LPS would not likely cross-react with another O determinant; thus organisms expressing a particular LPS may be distinguished from others by virtue of the somatic ("body") types.

In contrast, because of the conserved nature of the Lipid A or core region, different organisms that possess endotoxin or endotoxin-like entities will have antigenically similar regions. Thus, antibodies raised to these determinants will react with an entire class (group) of microorganisms, those of which can express LPS regardless of somatic type.

In Nature, the induction of anti-Lipid A or anti-core poly- saccharide reactive antibodies does not occur readily because of the existence of the somatic determinants attached thereto. However, there are known to exist in Salmonella mutations which affect various steps in the synthesis of the LPS/glycolipid molecule. Certain of these mutations result in strains which produce truncated forms of the LPS/glycolipid molecule and are known as R mutants. One of the most defective R types known is designated as Re. This mutant is well-known having been described by Stocker, et al. (J. Gen'l. Microbiol., 70: 527 (1972)) and is publically available from the Salmonella Stock Center, Dept. of Biology, University of Calgary, Calgary, Alberta, Canada.

As described herein it is possible to prepare antibodies which react specifically with the Lipid A or core-determinants thus providing valuable immunological reagents for the detection of a class of microorganism, i.e., those microorganisms expressing LPS/glycolipid regardless of somatic type.

A variety of protocols may be used to provide the Lipid A or core-polysaccharide reactive antibodies. Conventional immunization and isolation procedures result in the production and recovery of polyclonal antisera directed against the shared determinants of the LPS antigen. Alternatively, somatic cell hybridization procedures may be employed to construct hybridoma cell lines capable of generating monoclonal antibody to the determinants in question. These procedures are more fully described in the Examples which follow.

Although it has been recently demonstrated that conventional polyclonal sera raised to *Salmonella typhimurium* Re mutants cross-react with various Chlamydia species, (Nurminen, et al., Science 220: 1279–81 (1983)), there is no suggestion of the diagnostic utility nor of the wider reactive potential of the antibodies as produced and described herein.

It has been surprisingly discovered that the immunological reagents described herein not only react with Gram-negative bacteria expressing LPS such as Salmonella and Neisseria, but also all Chlamydia species as well. Predicated on this finding it is now possible to generate immunological reagents of extremely broad specificty such as a single antibody reactive with any and all LPS/glycolipid producing organism. Appropriate target organisms include Gram-reactive bacteria such as Salmonella, Brucella, Escherichia, Neisseria, Serratia, Pasteurella, Proteus, Shigella, Klebsiella, as well as Chlamydia, and Rickettsia.

Furthermore a group of immunological reagents of intermediate specificity are also disclosed herein. Antibodies of the group react specifically with members of all species within a given genera but not with organisms outside that genera. These antibodies are said to be genera-specific.

Thus, by using an antibody of broad specificity, it is possible to perform a single test for a large number of LPS producing organisms merely by reacting said antibody with a clinical sample and detecting any antibody-antigen reaction which occurred by measuring the antigen and antibody complex directly, conventionally by monitoring an analytically indicatable detection system.

Thus antibodies of the subject invention can be used directly and can be modified as necessary to render them useful in any of the well-known immunological detection systems. Although not meant to be exhaustive, suitable methods for detection of the antigen-antibody reaction include: precipitation, agglutination, double antibody techniques, fluoroscent-, enzyme-, ferritin-, or radioactively-labelled antibodies $^{125}$I-/ similarly radioactively labelled antibodies, protein A from *Staphylococcus aureus,* enzyme-linked immunoassay (ELISA) or biotin-based assay systems. The subject invention provides specific reagents for the reaction with the LPS/glycolipid antigen and not any particular method of indicating the resulting reaction product. The most appropriate method of indication can be determined by one skilled in the art. A wide variety of indicator systems are contemplated, and the subject invention should not necessarily be limited by a particular method of indicating the positive reaction.

In a preferred embodiment, the immunological reagent (the anti-Lipid or anti-core LPS reactive antibody of or monoclonal origin) is employed as a capture antibody in a "sandwich-type" assay as described in U.S. Pat. No. 4,376,110. According to this embodiment, the anti-Lipid A or core-reactive antibody is attached to a solid support by widely known cross-linking methods such as described by S. Avrameas In: *Immunoassays for the 80's* Voller et al. (Eds) University Park Press, Baltimore (1981) at page 85.

A clinical sample, which may be defined as body fluids or secretions such as blood, serum, saliva, stool, urine, milk, topical washing of skin or genitals, tissue samples or homogenates thereof and samples of culture fluids of infected cells or homogenates thereof, is reacted with the supported immunological reagent under conditions which promote the formation of an immune complex between said supported reagent and any material containing the Lipid A or core determinants, thereby binding to the support one or more members of a variety of taxonomic groups of micro-organisms. The specific identity of the constituent members of the bound population may be determined, after washing the initial reaction product to remove unbound contaminants, by subsequently reacting the bound population with specific antisera for each specific taxonomic type of interest e.g. genera-specific, species-specific or serotype-specific antisera. An advantage employing a reagent of broad specificty is that considerable research and development as well as production time and expense is saved by eliminating the necessity of generating a large number of reagents of narrower specificity to accomplish the same result.

In a further embodiment, the above described "sandwich" assay can be carried out by providing a plurality of separate reactions of the supported "capture" reagent followed by detection of the reacted sample by adding a particular genera-, species- or serotype-specific reagent to an individual reaction or alternatively two or more specific reagents may be added to a single reaction thus it is possible to detect simultaneously in one reaction two or more taxomonically distinct microorganisms. In this later variation of the assay, if the clinical sample contains both Chlamydia as well as Neisseria both organisms would be retrieved by the "capture" antibody attached to the solid support. Once bound, addition of two additional types of detectably labelled antibodies, one specific for Chlamydia and the other specific for Neisseria would permit the simultaneous detection of both organisms Detection is facilitated by employing analytically distinct reagents is labelling the specific antibody. For example, the Chlamydia specific antibody may be labelled with B-galactosedase and the product of the ELISA reaction measure of one spectrophotometric wavelength whereas the Neisseria specific antibody labelled with alkaline phosphatase and the ELISA reaction product measured at a second wavelength. Other variations employ colorimetric blending of two separate reaction products or the use of a radiometric/photospectrometric combination are also possible.

The following examples further illustrate various facets of the invention but are not to be viewed as limitations of the invention per se.

EXAMPLE 1

Methods for the Production and Recovery of Polyclonal Antibody to Endotoxic Glycolipids New Zealand white rabbits weighing approximately 2 kg and 8 to 10-week old BALB/c mice were injected subcutaneously with an emulsion containing equal parts of incomplete Freund's adjuvant and water in which was suspended formalin-fixed *Salmonella typhimurium* Re chemotype whole cells. Lyophilized whole cells were formalin fixed by suspension in 0.2% formaldehyde and incubation overnight at 25° C. They were diluted into water used for preparation of the emulsion for injection so that each rabbit received 1.0 mg and each mouse, 0.1 mg. The animals were injected subsequently with the same quantities of whole cells suspended in water and given intravenously at 2 to 6-week intervals for 3 to 6 months. The animals were anesthetized and exanquinated by cardiac puncture. Sera collected from the blood was stored frozen or filtered through 0.45 um filters and stored at 4° C. in 0.1% sodium azide. This antisera is termed anti-Re glycopid antisera.

Other rabbits and mice were immunized in a similar scheme but with whole cells treated with 1% acetic acid in water at 100° C. for 2 hr (Osborn, M.J., Proc. Nat. Acad. Sci. U.S.A. 50, 499 (1963) and coated with Lipid A. The acid treatment removes the KDO and core saccharides from endotoxin in the walls of the bacteria, leaving the lipid A region intact. Purified endotoxin extracted from lyophilized whole bacteria by the procedure of Galanos et al. (Eur. J. Biochem. 9, 245 (1969)) was also converted to Lipid A by treatment with acetic acid. This lipid A was adsorbed to the acetic acid-treated whole bacteria by mixing into a homogeneous suspension the lipid A and the acid-treated bacteria and then evaporating the water under reduced pressure at 50–60° C. until a thick slurry was generated.

Animals immunized with this antigenic preparation produced a sera termed anti-lipid A glycolipid antisera. In certain circumstances, some of the animals received an equal mixture of untreated whole cells and acid-treated, lipid A-coated whole cells. Sera from these mice is termed anti-Re-Lipid A glycolipid antisera.

These antisera were tested in an enzyme immunoassay for reactivity to purified endotoxic glycolipids (termed Re endotoxin or lipid A) prepared as described above. These glycolipids were attached to polystyrene plates by incubating 0.1 ml/well of a solution containing endotoxic glycolipid (25 ug/ml), triethylamine (0.5 ul/ml), sodium azide (0.15) and $MgCl_2$ (1 mM) for 6 to 18 hours at 37° C. This solution was removed and replaced with phosphate buffered saline (pH 7.4) containing 1 mM MgCl. The plates were stored at 4° C. The test antisera or normal rabbit sera or normal mouse sera at various dilutions (commonly 1/1000) was added to each well (100 ul/well after removal of the saline solution used for storage). The plates were incubated 3 to 18 hours at 25 or 37° C.; the sera was decanted; the plates were washed with buffered saline containing MgCl (three times, 200 ul each time); alkaline phophatase-conjugated antiserum to rabbit or mouse immunoglobulin ($IgG_1$ and IgM) (purchased from Tago Inc., Burlingame, CA) was added and incubated for 6 to 18 hours at 37° C. The plates were again washed as before and 100 ul of alkaline phosphatase substrate p-nitro-phenol phosphate in 1% diethylamine and 1 mM MgCl was added. The plates were examined visually for yellow color development or spectrophotometrically at 405 nm following incubation at 25° C. for ½–3 hours.

EXAMPLE 2

Antibody to Endotoxins of Chlamydia Species and Neiserria Species

Rabbits and mice were immunized with formalin-fixed elementary bodies of *C. trachomatis* (strain L2/434/Bu(L2) grown in HeLa cells (see Caldwell et al. Infect. Immun. 31, 1161 (1981) for preparation of purified elementary bodies). The formalin fixation and immunization scheme was as described in Example 1 above. Other animals were immunized with formalin-fixed *N. gonorrhea* (laboratory strain F62 phenotyped P++O+) in a similar immunization protocol.

Sera from these animals was tested for antibody reactivity in an immunoassay as described above in Example 1. Whole elementary bodies or endotoxic extracts *C. trachomatis* or whole bacteria *N. gonorrhea* were attached to polystyrene plates ($10^7$ organisms or equivalent extract per ml of phosphate buffered saline; 0.15 ml per well). The endotoxic extracts were obtained as described in Example 1. The plates were subsequently treated with MEM solution containing 10% fetal calf serum and 0.25% bovine serum albumin (0.25 ml per well). Some of the wells were treated with sodium metaperiodate (50 mM) in sodium acetate (50 mM, pH 5.6 for 3 hours at 37° C. This treatment destroys the immunological reactivity of certain sugars in the endotoxins or endotoxic glycolipids, but does not affect the immunological reactivity of peptides in proteins.

EXAMPLE 3

Monoclonal Antibody to Endotoxic Glycolipids

A. Female BALB/c mice were immunized with a mixture of untreated and acid-treated cells as described in Example 1. The mice received 4 to 6 injections of immunogen and were euthanized three days after the last injection. The spleens were removed aseptically and homogenized between glass microscope slides. The cells were washed in minimum essential medium (MEM) and the red blood cells lysed by treatment for 45 seconds in sterile water. The cells were diluted into MEM to stop the lytic process. The spleen cells remaining were pelleted at room temperature upon centrifugation for 15 minutes at 1500 rpm in a Beckman TJ-6 table top centrifuge. To this pellet was added 2 to $5 \times 10^7$ SP2/0 myeloma cells (Institute for Medical Research, Camden, N.J. 08103) that had been washed twice in MEM. Typically spleen cells from one spleen were combined with myeloma cells recovered from vigorously shaking three, 250 $cm^2$ Falcon tissue culture flasks used for maintenance of the myeloma cell line.

The combined spleen cells and myeloma cells were centrifuged for 10 minutes at 600 rpm in the Beckman TJ-6 centrifuge at room temperature. The pellet was dislodged after decanting the MEM. The cells were then treated for 1 minute with 1.0 ml of polyethylene glycol 4000 (Sigma Chemical Co.) which had been sterilized and diluted with an equal part of MEM just before use. It was important to dilute the polyethylene glycol with MEM while it was still hot from sterilization. It was cooled to 37° C. before addition to the spleen cell and myeloma cell pellet Sequential additions of 1.0, 2.0, and 4.0 ml of MEM followed at 1.0, 2.0, and 4.0 minute intervals. The fusion treatment was terminated by the addition of 43 ml of MEM with 10% fetal calf serum (Hyclone Laboratories, Sterile Systems, Logan, Utah) and Hypoxanthine, aminopterine, and thymidine (HAT). The cells were distributed into two, 24-well tissue culture trays. Fresh HAT media was added the following day, and twice weekly for two weeks. The cells were cultured an additional two weeks in hypoxantine- and thymidine-containing MEM and fetal calf serum. Wells supporting the growth of hybridomas covering approximately one third the surface area of the well were screened for antibody as described in Example 1 by the enzyme immunoassay procedure.

Generally, at 5 to 8 weeks following the fusion date, cells from positive wells were cloned by limiting dilution. The cells were diluted to 30 cells and 10 cells per ml of media; 0.1 ml of these solutions were dispensed in 96-well trays. An additional 0.1 ml of media containing spleen cells ($2.5 \times 10^6$ ml) was added; the trays were wrapped in plastic film and incubated at 37° C. in a humidified chamber in the presence of 5% $CO_2$ for 2 to 6 weeks. The wells were again screened for antibody production. A population was considered cloned when obtained from a well that was one of a group of wells receiving the same cell contractation only if that group had growth of hybridomas in one third or fewer wells. Generally clones were cloned 3 to 4 times to ensure single-cell origin.

Positive clones were transferred into 24-well tissue culture plates and after 1 to 3 weeks, into flasks in order to expand the populations. The culture supernatants were collected and stored at 4° C. in 0.1% sodium azide. Ascites were collected from BALB/c female mice to 4-8 weeks following being primed with pristine (0.5 ml i.p. 10 to 30 days before injection of hybridoma cells) and injected i.p. with $10^6$ to $10^7$ hybridoma cells B. In a modification of the above procedure, P3X63Ag8Z myeloma cells are substituted for the SP2/0 cells and substantially similar results are obtained

EXAMPLE 4

Solid Phase Immunometric Assay

The principle of detection of antigens (chlamydial endotoxin or chlamydia in this example) by a solid phase immunometric assay whereby the antigen is sandwiched between two antibodies is well documented (for review see *Immunoassays for the 80s,* A. Voller, A. Bartlett and D. Bidwell, eds. University Park Press, Baltimore (1981) at page 85. Heterogeneous enzyme immunoassays by S. Avrameas). The general scheme of such an assay is (1) adsorbtion or covalent linking of the first antibody to a solid phase such as a polystyrene or nylon tube, plate or bead, (2) incubation of the test material containing the antigen which will specifically bind to the first antibody, (3) washing away unreacted antigen(s) not specifically bound, (4) addition of the second antibody which will also react with the antigen already bound to the first antibody (the second antibody may be labelled by iodination with radioactive iodine, e.g., or by being conjugated with an enzyme such as alkaline phosphatase), (5) washing an unreacted labelled second antibody from the reaction vessel, and finally (6) measuring the presence of the labelled antibody remaining in the vessel (radiometrically or enzymatically).

The protocol used herein is after the procedure described by E. Engvall, K. Jonsson, and P. Perlmann (Biochim. Biophys. Acta 251, 427-434 (1971)). In brief the procedure was to coat polystyrene plates with polyclonal or monoclonal antibody to endotoxic glycolipids (see Example 1 and 2 for preparation of these antibodies). The antibody solutions were diluted in 0.1 M sodium carbonate buffer (pH 10) and 100 ul dispensed into each well of a 96-well polystyrene plate. They were incubated at 37° C. for 3 hours minimum (maximum of 18 hours), washed with phosphate buffered saline (pH 7.4) containing 0.9% sodium chloride and 0.05% Tween-20 and 0.5% bovine serum albumin, the test material containing chlamydia or endotoxic glycolipid antigens diluted in the same type solution as used for the wash step was added (100 ul per well), the plates were incubated a minimum of 3 hours at 37° C, washed as before (200 ul per well per wash, 4 washes at 3 minute intervals), the second labelled antibody (immunoglobulin conjugated to alkaline phosphatase by the procedure described by S. Avrameas (Immunochemistry 6, 43 (1969)) was added and incubated 3-18 hours at 37° C., the reaction vessels were washed as before, 100 ul of substrate solution containing p-nitro-phenol phosphate (Sigma Chemical Col., St. Louis, MO) (1 mg/ml) in 1% diethylamine and 1 mM $MgCl_2$ was added. The reaction was read visually after development of a distinct yellow color in positive reaction wells or quantified spectrophotometrically at 405 nm in a Beckman DU-8 spectrophotometer.

EXAMPLE 5

Antibody Reactivity in Enzyme Immunoassay

Protocol: The various antigens were coated on the surfaces of polystyrene plates as described in Example 1. The antisera and monoclonal antibody solutions were added and processed as described. The reactivity of these antibodies to the antigens were detected using alkaline phosphatase conjugated to anti-mouse or anti-rabbit immunoglobulins.

TABLE I

| Source of Antibody | Antigen coated on wells | | | | | | |
|---|---|---|---|---|---|---|---|
| | Not treated | | | | | Periodate treated | |
| | None | LA | Re GL | N.g. | C.t. | N.g. | C.t. |
| A. Polyclonal | | | | | | | |
| Rabbit anti-Re GL | − | − | ++ | ± | ++ | − | ± |
| Rabbit anti-LA | − | ++ | ± | ± | + | + | + |
| Mouse anti-Re-LA GL | − | ++ | ++ | ± | ++ | + | ++ |
| Mouse anti-C. trachomatis | − | − | − | − | ++ | − | + |
| Mouse anti-N. gonorrhoeae | − | − | − | ++ | − | + | − |
| Normal Rabbit sera | − | − | − | − | − | − | − |
| Normal Mouse sera | − | − | − | − | − | − | − |
| B. Monoclonal (mouse) | | | | | | | |
| Anti-Re GL (clone: | | | | | | | |
| Re-1) | − | − | ++ | ± | ++ | − | − |
| Re-2) | − | − | ++ | ± | ++ | − | − |
| Re-3) | − | − | ++ | ± | ++ | − | − |
| Anti-LA (clone: | | | | | | | |
| LA-1) | − | ++ | ± | − | − | − | + |
| LA-2) | − | ++ | ± | + | + | − | ++ |
| LA-3) | − | ++ | ± | − | ± | − | + |
| LA-4) | − | ++ | + | +. | + | ++ | ++ |
| LA-5) | − | ++ | + | + | + | ++ | ++ |
| Anti-C-GL (clone: | | | | | | | |
| C-1) | − | − | − | − | ++ | − | − |

TABLE I-continued

| Source of Antibody | Antigen coated on wells | | | | | | |
|---|---|---|---|---|---|---|---|
| | Not treated | | | | | Periodate treated | |
| | None | LA | Re GL | N.g. | C.t. | N.g. | C.t. |
| C-2 | − | − | − | − | ++ | − | − |
| C-3 | − | − | − | − | ++ | − | − |
| C-4 | − | − | − | − | ++ | − | − |
| C-5 | − | − | − | − | ++ | − | − |

Abbreviations:
(1) N.g. = *Neiserria gonorrhoeae* whole cells
(2) C.t. = *Chlamydia trachomatis* elementary bodies
(3) LA = Lipid A
(4) Re GL = Re endotoxic glycolipid
(5) C-Gl = *Chlamydia glycolipid*
"−" (negative) = Absorbancy at 405 mm below 0.1
(6) "+" (positive) = Absorbancy between 0.31 & 0.5
"++" (positive) = Absorbancy greater than 0.5
"±" (weakly positive) = between 0.1 & 0.30

From the above data it can be seen that both polyclonal and monoclonal antisera can be generated that will react with endotoxic glycolipids from a variety of sources. Both anti-Re glycolipid antisera and anti-Lipid A antisera reacts with periodate-sensitive determinates in *C. trachomatis* elementary bodies. Weak reactivity of these antisera is seen to *N. gonorrhoeae*. The periodate-sensitivity of certain of these reactions is evidence that the determinate recognized by these antisera is the endotoxic glycolipid present in the cell walls of the microbes. The antisera are defined by their reactivity to purified endotoxic glycolipid and Lipid A from Salmonella whole cells. However, these antisera contain antibodies to to other non-endotoxic molecules in the whole cells such as proteins. Only the anti-endotoxic glycolipid antibodies bind to the chlamydial and gonococcal microbes and this binding is in certain cases prevented by pretreating the microbes with periodate which destroys the unprotected sugars of the endotoxic glycolipids within the whole cells or elementary bodies. However, if the epitope comprises a chemically modified sugar (e. g. amino sugars) the periodate treatment is ineffective.

Monoclonal antibodies with reactivity similar to the polyclonal antisera can also be generated. This reactivity, too, in certain cases is periodate-sensitive, thereby providing further evidence that the epitopes being recognized on the *C. trachomatis* and *N. gonorrhoeae* are the sugar moieties of the endotoxic glycolipids in the cell walls or membranes. In addition, these moieties are immunologically identical as defined by monoclonal antibody reactivity to some of the sugar moieties in the endotoxic glycolipids of the core or Lipid A region of gram negative bacteria.

Certain of the clones described in Table I were deposited with the American Type Culbum Collection 12301 Parklawn Drive, Rockville, Md. on Jan. 19, 1984 and the requisite fees were paid. Access to the cultures will be available during the pendency of the patent application to one determined by the Commissioner to be entitled thereto under 27 CFR §1.14 and 35 USC. §122. All restrictions on availability of said culture to the public will be irrevocably removed upon the granting of the instant application and said culture will remain permanently available during the term of said patent. Should the culture become nonviable or be inadvertently destroyed, it will be replaced with viable culture(s) of the same taxonomic description.

Each deposited clone was serotyped and assigned the accession number as shown in Table II.

TABLE II

| Clone | | Antibody Type | Accession No. |
|---|---|---|---|
| Anti-Re GL | Clone Re-1 | IgG$_3$ (K) | HB8482 |
| Anti-Re GL | Clone Re-2 | IgG$_3$ (K) | HB8481 |
| Anti-LA | Clone LA-4 | IgM (K) | HB8480 |
| Anti-LA | Clone LA-5 | IgM (K) | HB8479 |
| Anti-C GL | Clone C-2 | IgG$_{2a}$ (K) | HB8478 |

What is claimed is:

1. An immunological reagent for the detection of two more endotoxin lipopolysaccharide/glycolipid antigen producing microorganisms comprising a monoclonal antibody specifically reactive with shared antigenic determinatnts of said lipopolysaccharide/glycolipid antigen said determinants being selected from the group consisting of the Lipid A region and core oligosaccharide region of said lipopolysaccharide/glycolipid antigen and said antibody being produced by a hybridoma selected from the group consisting of clones Re-1 (ATCC No. HB 8482), Re-2 (ATCC No. HB 8481), LA-4, (ATCC No. HB 8480), LA-5 (ATCC No. HB 8479) and C-2 (ATCC No. HB 8478).

2. A method for the immunological detection of an antigen shared by a plurality of taxonomically distinct microorganism comprising:

contacting a sample containing said microorganisms or antigens thereof with an analytically indicatable antibody to form an immunocomplex of said microorganism or antigen thereof and said antibody, said antibody being characterized as being monoclonal antibody having affinity for an antigenic determinant shared by aaid microorganism wherein said determinant is selected from the group consisting of the Lipid A region and core-oligosaccharide region of an antigen associated with endotoxin molecules and said antibody being produced by a hybridoma selected from the group consisting of n=−1 (ATCC No. HB 8482), Re-2 (ATCC No. HB 8481), LA-4 (ATCC No. HB 8480), LA-5 (ATCC No. HB 8479) and C-2 (ATCC No. HB 8478).

3. The method according to claim 2 wherein said antibody is analytically detected by fluorometric, enzymatic or radiometric measurement of fluorescent, enzymatic or radioactive material, chemically complexed with said antibody.

4. The method according to claim 2 wherein said indicatable antibody is analytically indicated by reaction with a second antibody specific for said indicatable antibody, said reaction being indicated by fluorometric, enzymatic or radiometric measurement of fluoroscent, enzymatic or radioactive material chemically complexed to either of said antibodies.

5. The method according to claim 2 wherein said region is the Lipid A region.

6. The method according to claim 2 wherein said region is the core-oligosaccharide region.

7. The method according to claim 2 wherein said sample is a clinical sample selected from the group consisting of blood, serum, saliva, stool, urine, milk, topical washing of skin or genitals, tissue samples or homogenates thereof and samples of cell culture fluids of infected cells or homogenates thereof.

8. In a two-site immunometric assay to identify an antigen in a sample comprising forming a ternary complex of a first labelled antibody, said antigen, and a second antibody said second antibody being bound to a solid carrier insoluble under ternary complex forming conditions wherein the presence of the antigen is detected and identified by measuring either the amount of labelled antibody bound to said solid carrier or the amount of unreacted labelled antibody: the improvement comprising employing as said second antibody a monoclonal antibody characterized in having affinity for an antigenic determinant site of said antigen which is shared by a plurality of taxonomically distinct microorganisms said determinant being selected from the group consisting of the Lipid A region and core oligosaccharide region of an antigen assocated with endotoxin molecules and said antibody being produced by a hybridoma selected from the group consisting of clones Re-1 (ATCC No. HB 8482), Re-2 (ATCC No. HB 8481), LA-4, (ATCC No. HB 8480), LA-5 (ATCC No. HB 8479) and C-2 (ATCC No. HB 8478).

9. The method according to claim 8 wherein said region is the Lipid-A region.

10. The method according to claim 8 wherein said region is the core oligosaccharide.

11. The method according to claim 8 wherein said antigenic determinant site reactive with said first antibody and said antigenic determinant site reaction with said second antibody are regions of the same macromolecule.

12. The method according to claim 11 wherein said antigenic determinant site reaction with said first antibody is comprised of the somatic region of an endotoxic lipopolysaccharide.

13. The method according to claim 11 wherein said antigenic determinant site reactive with said second antibody and said antigenic determinant site reactive with said first antibody are regions of separate macromolecules.

14. The method according to claim 13 wherein said antigenic determinant site reactive with said second antibody is the Lipid A or core oligosaccharide region of a lipopolysaccharide/glycolipid antigen associated with endotoxin molecules.

15. The method according to claim 13 wherein said antigenic determinant site reactive with said first antibody is a region of any nonendotoxic lipopolysacchride molecule with the proviso that said determinant is specific to a taxonomically distinct microorganism.

16. The method according to claim 11 wherein said first labelled antibody is labelled with a fluorometric, enzymatic or radioactive material.

17. A monoclonal antibody produced by a hybridoma formed by a fusion of cess from a mouse myeloma and spleen cells from a mouse previously immunized with Salmonella Re endotoxin glycolipid whereins said hybridoma is selected from the group consisting of Clone Re-1 (ATCC No. HB 8482) and Re-2 (ATCC No. 8481).

18. A monoclonal antibody produced by a hybridoma, formed by a fusion of cells from a mouse myeloma and spleen cells from a mouse previously immunized with Lipid A wherein said hybridoma is selected from the group consisting of Clon LA-4 (ATCC No. HB 8480) and LA-5 (ATCC No. HB 8479).

19. The monoclonal antibody produced by the hybridoma is Clone C-2 (ATCC. No. HB 8478).

20. A kit for use in the immunological detection of an antigen shared by a plurality of taxonomically distinct microorganisms comprising antigen reactive means comprising a monoclonal antibody specifically reactive with said antigen, said antigen possissing antigenic determinants selected from the group consisting of the Lipid A region and core oligosaccharide region of an antigen associated with endotoxin molecules, said antibody being further characterized in being chemically complexed with an analytically detectable reagent and being produced by a hybridoma selected from the group consisting of clones Re-1 (ATCC No. HB 8482), Re-2 (ATCC No. HB 8481), LA-4, (ATCC No. HB 8480), LA-5 (ATCC No. HB 8479) and C-2 (ATCC No. HB 8478).

21. The kit of claim 20 wherein said reagent comprises fluorescent, enzymic or radioactive material.

22. The kit of claim 21 wherein said reagent is the enzyme alkaline phosphatase.

23. The kit of claim 20 wherein said antibody is the monoclonal antibody produced by a hybridoma selected from the group consisting of Clone Re-1 (ATCC No. HB 8482) and Re-2 (ATCC No. HB 8481).

24. The kit of claim 20 where said antibody is the monoclonal antibody produced by a hybridoma selected from the group consisting of Clone LA-4 (ATCC No. HB 8480) and LA-5 (ATCC No. HB 8479).

25. The kit of claim 20 wherein said antibody is the monoclonal antibody produced by the hybridoma Clone C-2 (ATCC No. HB-8478).

26. A kit for use in the immunological detection of two or more lipopolysaccharide/glycolipid antigen associated with endotoxin molecules producing microorganisms comprising:
(1) a lipopolysaccharide reactive means comprising a first monoclonal antibody specifically reactive with, an antigenic determinant selected from the group consisting of the Lipid A region and core oligosaccharide region of an antigen associated with endotoxin molecules, said antibody being produced by a hybridoma selected from the group consisting of clones Re-1 (ATCC No. HB 8482), Be-2 (ATCC No. HB 8481), LA-4, (ATCC No. HB 8480), LA-5 (ATCC No. HB 8479) and C-2 (ATCC No. HB 8478) and
(2) a second antibody specifically reactive with said first antibody, said second antibody being further characterized in having chemically complexed thereto an analytically detectable reagent.

27. The kit of claim 26 wherein said reagent comprises fluoroscent, enzymic, or radioactive material.

28. The kit of claim 27 wherein said reagent is the enzymic alkaline phosphatase.

29. The kit of claim 26 wherein said first antibody is the monoclonal antibody produced by a hybridoma selected from the group consisting of Clone Re-1 (ATCC No. HB 8482) and Re-2 (ATCC No. HB 8481).

30. The kit of claim 26 wherein said first antibody is the monoclonal antibody produced by a hybridoma selected from the group consisting of Clone LA-4 (ATCC No. HB 8480) and LA-5 (ATCC No. HB 8479).

31. The kit of claim 26 wherein said first antibody is the monoclonal antibody produced by the hybridoma Clone C-2 (ATCC No. HB-8478).

32. A kit for use in a two-site immunometric assay for the identification of a plurality of taxonomically distinct lipopolysaccharide producing microorganisms comprising:
(1) a first lipopolysaccharide reactive means comprising a first antibody specifically reactive with an antigenic determinant of said lipopolysaccharide said determinant being specific to a taxonomically distinct microorganism, said first antibody being further characterized in having chemiclaly complexed thereto an analytically detectable reagent, and
(2) a second lipopolysaccharide detecting means comprising a second monoclonal antibody specifically reactive to an antigenic determinant of lipopolysaccharide, selected from the group consisting of the Lipid A region and core oligosaccharide region, said antibody being produced by a hybridoma selected from the group consisting of clones Re-1 (ATCC No. HB 8482), Re-2 (ATCC NO. HB 8481), LA-4, (ATCC No. HB 8480), LA-5 (ATCC No. HB 8479) and C-2 (ATCC No. HB 8478).

33. The kit of claim 32 wherein said reagent comprises fluoroscent, enzymic, or radioactive material.

34. The kit of claim 33 wherein said reagent is the the enzyme alkaline phosphataste.

35. The kit of claim 32 wherein said microorganisms are selected from the group consisting of Escherichia, Salmonella, Brucella, Neiserria, Chlamydia, and Rickettsia.

36. The kit of claim 32 wherein said second antibody is the monoclonal antibody produced by a hybridoma selected from the group consisting of Clone Re-1 (ATCC No. HB 8482) and Re-2 (ATCC No. HB 8481).

37. The kit of claim 32 wherein said second antibody is the monoclonal antibody produced by a hybridoma selected from the group consisting of Clone LA-4 (ATCC No. HB 8480) and LA-5 (ATCC NO. HB 8479).

38. The kit of claim 32 wherein said second antibody is the monoclonal antibody produced by the hybridoma Clone C-2 (ATCC No. HB-8478).

* * * * *

UNITED STATES PATENT AND TRADEMARK OFFICE
CERTIFICATE OF CORRECTION

PATENT NO. : 4,683,196

DATED : July 28, 1987

INVENTOR(S) : Charles McLaughlin

It is certified that error appears in the above-identified patent and that said Letters Patent is hereby corrected as shown below:

In the Abstract, line 4: "iwth" should read --with--

Column 6, line 36: "organisms Detectyion" should read --organisms. Detection--

Column 8, line 48: "pellet Sequential" should read --pellet. Sequential--

Column 12, line 50, Claim 2: "aaid" should read --said--

Column 12, line 56, Claim 2: "n=1" should read --Re-1--

Column 16, line 6, Claim 33: "fluoroscent" should read --fluorescent--

UNITED STATES PATENT AND TRADEMARK OFFICE
CERTIFICATE OF CORRECTION

PATENT NO. : 4,683,196

DATED : July 28, 1987

INVENTOR(S) : Charles McLaughlin

It is certified that error appears in the above-identified patent and that said Letters Patent is hereby corrected as shown below:

Column 14, line 66, Claim 17: "sess" should read as --cells--

Column 14, line 16, Claim 20: "possissing" should read as --possessing--

Column 14, line 54, Claim 26: "Be-2" should read as --Re-2--

Column 14, line 62, Claim 27: "fluoroscent" should read as --fluorescent--

Column 15, line 17, Claim 32: "chemiclaly" should read as --chemically--

Signed and Sealed this

Seventeenth Day of May, 1988

Attest:

DONALD J. QUIGG

Attesting Officer
Commissioner of Patents and Trademarks

UNITED STATES PATENT AND TRADEMARK OFFICE
CERTIFICATE OF CORRECTION

PATENT NO. : 4,683,196
DATED : July 28, 1987
INVENTOR(S) : Charles McLaughlin

Page 1 of 2

It is certified that error appears in the above-identified patent and that said Letters Patent is hereby corrected as shown below:

Column 2, line 17: "typhimuruin" should read as --typhimurium--

Column 3, line 20: "Chyamdia" should read as --Chlamydia--

Column 5, line 17: "specificty" should read as --specificity--

Column 5, line 56: "anti-Lipid" should read as --anti-Lipid A--

Column 6, line 38: "reagents is labelling" should read as --reagents in labelling--

Column 7, line 5: "glycopid" should read as --glycolipid--

Column 7, line 10: "(1963)" should read as --(1963))--

Column 7, line 34: "(0.15)" should read as --(0.15 mg/ml)--

UNITED STATES PATENT AND TRADEMARK OFFICE
CERTIFICATE OF CORRECTION

PATENT NO. : 4,683,196
DATED : July 28, 1987
INVENTOR(S) : Charles McLaughlin

Page 2 of 2

It is certified that error appears in the above-identified patent and that said Letters Patent is hereby corrected as shown below:

Column 7, line 67: "animals was tested" should read as --animals were tested--

Column 8, line 10: "(50mM," should read as --(50mM)--

Column 8, line 58: "hypoxantine-" should read as --hyopxanthine--

Column 9, line 6: "contractation" should read as --contraction--

Column 11, line 32: "bodies to to other" should read as --bodies to other--

Signed and Sealed this

Thirteenth Day of September, 1988

*Attest:*

DONALD J. QUIGG

*Attesting Officer*      *Commissioner of Patents and Trademarks*